(12) United States Patent
Balasubramanian

(10) Patent No.: US 8,349,794 B2
(45) Date of Patent: Jan. 8, 2013

(54) RECONSTITUTION MEDIUM FOR PROTEIN AND PEPTIDE FORMULATIONS

(75) Inventor: Sathyamangalam V. Balasubramanian, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 1046 days.

(21) Appl. No.: 12/204,922

(22) Filed: Sep. 5, 2008

(65) Prior Publication Data

US 2009/0062205 A1 Mar. 5, 2009

Related U.S. Application Data

(62) Division of application No. 10/911,865, filed on Aug. 5, 2004, now abandoned.

(60) Provisional application No. 60/492,582, filed on Aug. 5, 2003.

(51) Int. Cl.
*C07K 14/00* (2006.01)
*A61K 38/00* (2006.01)

(52) U.S. Cl. ............................................. 514/2; 424/450

(58) Field of Classification Search ........................ None
See application file for complete search history.

(56) References Cited

U.S. PATENT DOCUMENTS

| | | | |
|---|---|---|---|
| 4,127,502 A | 11/1978 | Li Mutti et al. | |
| 4,795,806 A | 1/1989 | Brown et al. | |
| 5,580,856 A * | 12/1996 | Prestrelski et al. | 514/1.1 |
| 6,593,294 B1 | 7/2003 | Baru et al. | |
| 2002/0098192 A1 | 7/2002 | Whitlow et al. | |
| 2002/0132982 A1 | 9/2002 | Balasubramanian et al. | |
| 2003/0118539 A1 | 6/2003 | Fahl et al. | |
| 2003/0176331 A1 | 9/2003 | Rosenblum et al. | |
| 2004/0229793 A1 | 11/2004 | Balasubramanian et al. | |

FOREIGN PATENT DOCUMENTS

| | | |
|---|---|---|
| WO | WO9955306 A1 | 11/1999 |
| WO | WO0243665 A2 | 6/2002 |

OTHER PUBLICATIONS

Kirby, Christopher J., et al, Preparation of Liposomes Containing Factor VIII for Oral Treatment of Haemophilia, J. Microencapsulation, 1984, 33-45, vol. 1, No. 1.
Lenting, Peter J., et al., The Light Chain of Factor VIII Comprises a Binding Site for Low Density Lipoprotein Receptor-related Protein, The Journal of Biological Chemistry, Aug. 20, 1999, 23734-23739, vol. 274, No. 34, The American Society for Biochemistry and Molecular Biology, Inc., United States.
Raut, S., et al., Phospholipid Binding of Factor VIII in Different Therapeutic Concentrates, British Journal of Haematology, 1999, 323-329, 107, Blackwell Science Ltd.
Aguilar, Leopoldo, et al., Phospholipid Membranes Form Specific Nonbilayer Molecular Arrangements that are Antigenic, The Journal of Biological Chemistry, Sep. 3, 1999, 25193-25196, vol. 274, No. 36, The American Society for Biochemistry and Molecular Biology, Inc., United States.
Manning, Mark C., et al., Stability of Protein Pharmaceuticals, Pharmaceutical Research, 1989, vol. 6, No. 11, Plenum Publishing Corporation.
Balasubramanian, Sathyamangalam V., et al., Liposomes as Formulation Excipients for Protein Pharmaceuticals: A Model Protein Study, Pharmaceutical Research, 2000, vol. 17, No. 3, Plenum Publishing Corporation.
Braun, Andrea, et al., Protein Aggregates Seem to Play a Key Role Among the Parameters Influencing the Antigenicity of Interferon Alpha (IFN-$\alpha$) in Normal and Transgenic Mice, Pharmaceutical Research, 1997, vol. 14, No. 10, Plenum Publishing Corporation.

* cited by examiner

*Primary Examiner* — Anand Desai
(74) *Attorney, Agent, or Firm* — Hodgson Russ LLP

(57) ABSTRACT

Compositions useful for reconstitution of concentrated formulations containing protein/peptide pharmaceuticals are provided. The composition generally includes one or more lipids, as well as one or more alcohols that promote and stabilize the formation of (a) lipid molecular assemblies with greater protein encapsulation; (b) protein-lipid complexes and (c) protein and lipid solutions. The reconstitution medium improves the protein-lipid association that in turn alters the pharmaceutical properties.

11 Claims, 4 Drawing Sheets

RECONSTITUTION MEDIUM FOR PROTEIN AND PEPTIDE FORMULATIONS

This application is a divisional of U.S. non-provisional Ser. No. 10/911,865, filed Aug. 5, 2004, now abandoned which in turn claims priority to U.S. provisional application Ser. No. 60/492,582, filed on Aug. 5, 2003, the disclosures of which are incorporated herein by reference.

This work was funded by a grant no. RO1 HL70227-01 from the National Institutes of Health. The Government has certain rights in the invention.

FIELD OF THE INVENTION

This invention relates to compositions for reconstitution of freeze-dried formulations and more particularly provides a composition and method for reconstitution of freeze-dried formulations comprising proteins and lipids.

BACKGROUND OF THE INVENTION

Advances in protein engineering and biotechnology, have led to large scale production of proteins and peptides for pharmaceutical purposes such as replacement therapies and vaccines. However, due to their complex structure and folding dynamics, proteins undergo physical and chemical instability. These instabilities present unique difficulties in the production, formulation, storage and administration of protein pharmaceuticals (1,2). Chemical instability is related to covalent modification of the protein that leads to loss of activity. One strategy to overcome this difficulty and to prolong the shelf life, is to freeze dry protein products and reconstitute them prior to the administration. The reconstitution buffer is generally provided by the manufacturer. However, unique handling procedures need to be followed to avoid physical instability, as the reconstitution involves agitation, formation of foam and froth and the exposure of proteins to air-aqueous interface. Physical instability is related to protein folding at the molecular level, and denaturation, surface adsorption, aggregation, and precipitation are frequent manifestations of physical instability (1-3). Such instabilities complicate the safety of protein products as the presence of aggregates evokes undesired immune response (4). The loss of protein due to surface adsorption and binding to vial and syringes complicates the therapy. In order to avoid surface adsorption, it is a general practice to include large quantities of albumin but inclusion of such excipients presents other pharmaceutical problems including the safety related to the source of albumin.

SUMMARY OF THE INVENTION

In order to prevent physical instability, a strategy has been proposed to add lipidic particles to stabilize the intermediate structures. With this invention, we report the composition of a reconstitution medium which promotes the association of protein and lipid, in solution, to form stabilized lipidic molecular assemblies (cochleate, laminar, or other tertiary structures), protein-lipid bilayer complexes and protein-lipid solutions (in which lipids associate with hydrophobic protein domains without forming larger structures) by promoting protein-lipid interactions. Compositions and buffer conditions for preparing the reconstitution solution are disclosed. An example is low concentration of ethanol (less than about 60%, preferably 5-10% vol/vol) in various buffer systems. Another example is a solution comprising 0.5 to 10 mM $CaCl_2$. The reconstitution of the protein in such medium promotes the interaction of protein with lipidic structures, improving pharmaceutical properties such as stability, pharmacokinetic/pharmacodynamic characteristics and immune response. Such stabilized solutions have many biotechnology applications including replacement therapies and vaccines.

DETAILED DESCRIPTION OF THE INVENTION

Figure 1:
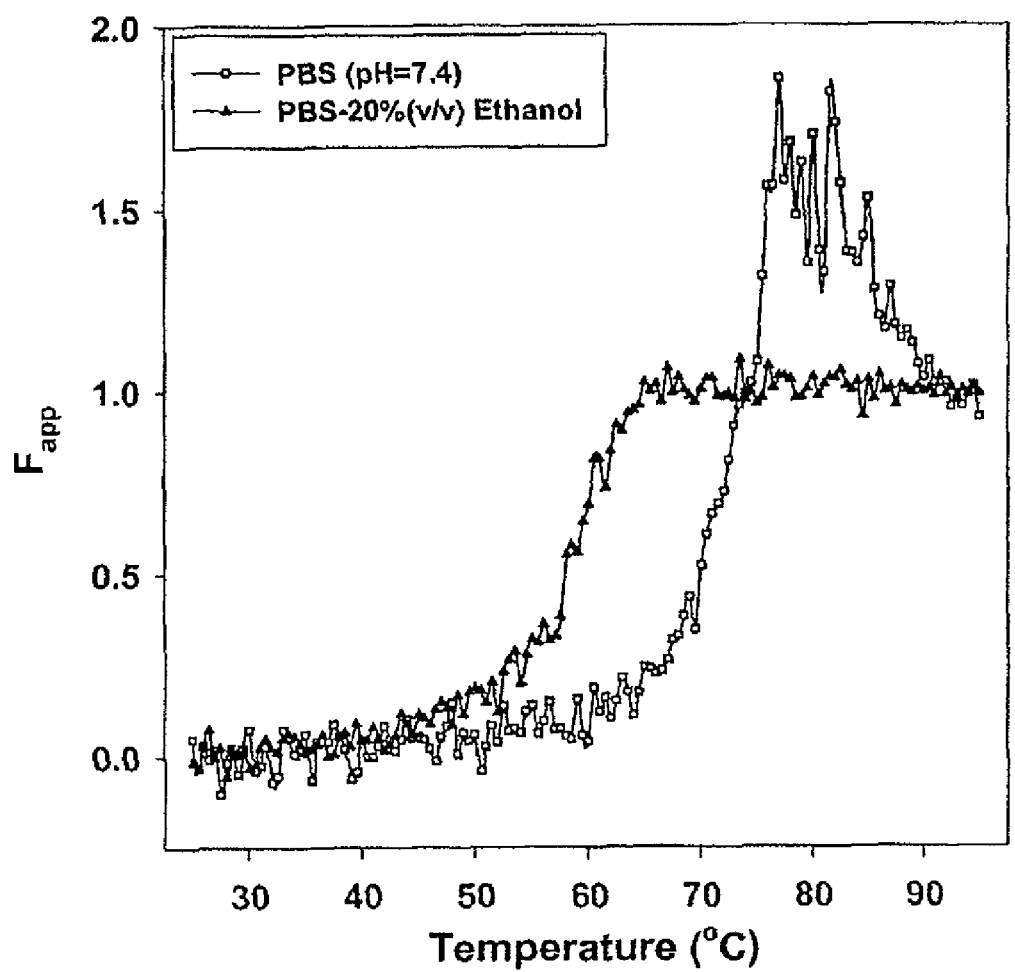
FIG. 1 displays the interaction of reconstitution medium with protein. The melting profile of lysozyme in the presence and absence of 20% ethanol in Phosphate buffered saline.

The present invention is directed to compositions for media useful in the reconstitution of dried protein formulations, and the method of use of such compositions. The compositions can be used with dry protein preparations, such as freeze-dried preparations containing protein to form structurally stabilized protein solutions. Furthermore, when lipids are included, the compositions promote the interaction between the protein hydrophobic domains and the lipid, forming solutions of structurally stabilized, non-aggregating, non-adhering protein/lipid solutions.

Alcohols are frequently added as excipients in the formulation of small, conventional organic drug molecules to improve stability and solubility. Intravenous preparations containing up to 50% ethyl alcohol are available for human use (5-7). However, to our knowledge, alcohols are not used in parenteral preparations which include proteins.

The present invention demonstrates that alcohols such as ethyl alcohol can be used as excipients for protein formulations and processing containing lipids. It has been discovered that concentrations of alcohol which are below a critical concentration, roughly 60 percent by volume in the case of some common alcohols, such as ethanol, for example, have the effect of structurally stabilizing proteins without greatly impeding their function. However, above the critical concentration, the alcohol induces significant changes in secondary and tertiary structure as demonstrated by the circular dichroism data in Examples 1 and 2, respectively. Such structural changes can be expected to affect the protein's function. Thus, in one embodiment, the present invention provides a stabilized protein solution which is buffered to a physiological pH and which comprises an alcohol at a concentration which is less than 60% by volume and one or more proteins.

Stabilization can be determined by methods which probe secondary and tertiary structure such as the disruption of circular dichroism spectra. If circular dichroism bands due to secondary structure are undisrupted, and all of the circular dichroism spectral bands due to tertiary structure are present, it can be inferred that little or no secondary and tertiary structure degeneration has taken place.

Furthermore, when a lipid component is included in the formation of solutions which contain alcohol, the alcohol component promotes the interaction between the protein and the lipid. Protein and lipid can associate in numerous ways to form complexes as simple as the combination of one or a few lipid molecules with hydrophobic protein sites or as complex as phospholipid bilayer, cochleate and other higher order structures. Without desiring to be bound by theory, it is thought that alcohols, such as, for example, ethanol, promote the exposure of hydrophobic domains, thereby lowering the free energy of the lipid/hydrophobic association. Moreover, protein/lipid complexes are stabilized because packing defects are induced and stabilized by alcohol molecules (Example 4), thus decreasing the free energy of the protein embedded in lipid complex. This effect can promote the interaction of protein (exposed hydrophobic domains) with lipid bilayer (packing defects) increasing the encapsulation efficiency of proteins in lipid complexes. Thus, in another embodiment the present invention provides a stabilized protein solution which is buffered to a physiological pH and which comprises one or more lipids, an alcohol at a concentration which is less than 60% by volume, and one or more proteins.

In addition to hydrophobic force mediated protein association with lipid molecular assemblies, the association of proteins with a specific lipid can be a result of electrostatic interaction This electrostatic component makes some protein/lipid associations particularly stable. For example, FVIII and phosphatidyl serine can associate by electrostatic interaction, and their pairing is thus particularly preferred. The complex may be further stabilized by hydrophobic forces promoted by the formulations of the present invention which lead to the formation of lipid molecular assemblies such as micelles, liposomes and cochleates.

Other advantages of using alcohol as an excipient are apparent in contexts in which a protein could become denatured and aggregate in solution, posing an immunological hazard to a person to whom the protein solution is to be parenterally administered. Additionally, some proteins, denatured proteins in particular, have a propensity to adhere to glass and other surfaces with which they may come into contact.

It has been found that the presence of alcohol can prevent the aggregation of protein in solution and adhesion of the protein to surfaces. The effect can be observed regardless of whether or not the protein is denatured. For example, during the processing and storage of freeze dried protein which results in denaturation of the protein, a reconstitution medium containing low alcohol concentrations may prevent the surface adsorption and aggregation of the protein. Further, denaturation during reconstitution due to agitation, shaking, formation of foam and froth and the contact of the protein with air-aqueous interfaces may be minimized by alcohol exposure. The anti-aggregant, anti-adherent effect of the formulations of the present invention is illustrated in Example 3.

The reconstitution of the dry protein preparation may be accomplished in several ways. If it is desired, the dry protein preparation can be combined with a lipid component (0.3 mM to about 4 mM) by combining both protein and lipid, either or both in dry or solvated form before the introduction of alcohol.

Thus in another embodiment, the present invention provides a method for reconstituting a dry protein or dry protein preparation to produce a stabilized protein solution which comprises addition of lipidic particles to said protein preparation to form a solution comprised of protein and lipid, and combining said solution with a reconstitution medium, said reconstitution medium comprising alcohol and being buffered to a physiological pH, such that less than about 30% of the dissolved protein aggregates.

It may also be convenient to directly reconstitute a dry protein preparation which is comprised of protein and lipid which are associated to form protein/lipid complexes, such as the product formed by freeze-drying a solution comprised of such complexes. In a further embodiment, the present invention provides a method for the reconstitution of a dry protein/lipid preparation to produce a stabilized protein solution comprising combining a dry protein preparation in which protein and lipid which are associated to form protein/lipid complexes with a reconstitution medium, said reconstitution medium comprising alcohol and being buffered to a physiological pH, such that less than about 30% of the dissolved protein forms aggregates.

In another embodiment, the reconstitution medium with and without ethanol comprises one or more lipids and calcium ions. Suitable concentrations of calcium are 0.5 to 10 mM and preferable concentration is about 5 mM.

It is thought that buffer salts play a prominent role in the stabilizing of protein/lipid interactions. In particular, calcium-containing buffers play a role in the stabilization of micellar structures, and are preferred in cases in which micellar structures are preferred over 1) other types of complexes or 2) lower order associations. Conversely, when associative structures other than micellar structures are preferred, such as when a solution is to be administered to a human or animal subject and large structures would trigger an immune response, it is desirable to either lower the calcium ion concentration, or use buffers which contain little or no calcium. The anti-aggregant, anti-adherent effects of the compositions of the present invention will be realized with other buffers as known in the art.

By "physiological pH," it is meant that the pH should be in the range which is conducive to the functioning of biological systems, such as, for example, in the range of from about 7.0 to about 7.4. A common physiological pH is about 7.2.

Degree of aggregation can be determined by a number of methods. Light scattering methods and size exclusion chromatography are examples of methods which can be used. Due to the range of error inherent in the size exclusion chromatography method, the percent aggregation as determined by size exclusion chromatograph refers to the average value in the range of error.

In general, the various ways of combining elements to create a stabilized solution are not material to realizing the benefits of the invention. The dried protein preparation may contain amounts of lipid, and may even be a preparation in which the lipid component is already associated with the protein as individuals/small groups or as higher order structures such as phospholipid bilayer, lamellar or cochleate structures. The lipid component can also be introduced either as part of a reconstitution solution containing the alcohol component or after the dry preparation has been reconstituted with the alcohol-containing reconstitution medium. If desired, the alcohol may be added to the solution after 1) a reconstituted protein solution has been formed, and 2) the lipid component has been added.

The dried protein preparation is most conveniently combined with the protein as a freeze dried or lyophilized preparation. It should be noted, however, that a stabilized solution can be formed from protein which has not been subjected to a drying process. Thus the benefits of the inventive medium extend not only to reconstituted solutions which have been prepared from dry protein, but also to solutions which have been formed from proteins introduced as emulsions, suspensions, or other non-desiccated forms.

The proteins which can be used in the compositions and methods of the present invention need only have hydrophobic domains which are accessible. By accessible, it is not meant that the hydrophobic domains must always be at the outer surface of the protein, but the protein must have hydrophobic domains such that when the protein is in the reconstitution medium, the domains can be positioned, through changes in protein conformation, such that they can contact lipids which are part of the medium. The proteins which can be used in the methods and compositions of this invention can range greatly in size, from peptides having fewer than fifty amino acids and weighing several kDa, to much larger proteins, such as a lysozyme or FVIII, with molecular weights in excess of 200 kilodaltons.

The lipidic molecules which can be used in the compositions and methods of the present invention can vary widely. Phospholipids such as phosphatidyl serine and phosphatidyl choline give excellent results. However, in addition to aliphatic lipids, lipids containing groups having other structures, such as multi-ringed structures including cholesterol can be used for protection against aggregation. In general, the lipid groups need only be long enough to interact with hydrophobic domains and stabilize, through these interactions, protein conformations in which the hydrophobic domains are exposed.

The present invention provides compositions comprising alcohols. When the compositions are to be used to reconstitute formulations intended for administration to humans or animals, the alcohols should be such that they can be safely administered. Such alcohols include ethanol, glycerol and polyethylene glycol (PEG). Other alcohols, such as sugar alcohols, which can be used include sucrose, glucose, mannitol, and trehalose. Some alcohols, such as benzyl alcohol, have been shown to have some stabilizing effect on lipid/protein solutions, but their toxicity to humans makes them of questionable value, except possibly at extremely low concentrations.

The alcohol concentration is less than about 60% vol/vol, preferably less than about 20% vol/vol, and even more preferably between about 5 and 10% vol/vol, where vol/vol refers to the ratio of volume of alcohol to total solution volume (including alcohol) at standard temperature and pressure.

The protein to lipid ratio can be in the range of from about 1:10 to about 1:1 million mol/mol. Preferred is a ratio in the range of from about 1:10 to about 1:100,000 mol/mol. A ratio in the range of from about 1:30 to about 1:10,000 mol/mol is most preferred.

Buffers can be used in concentrations in the range of from about 0.5 to 600 mM, with a preferred range of from about 5 to about 600 mM for NaCl and from about 0.5 to about 10 mM for $CaCl_2$.

In a reconstitution solution, the lipid concentration should be in the range of from about 0.3 mM to about 40 mM and preferably in the range 1 mM to 10 mM.

The addition of an alcohol can have an anti-aggregant, anti-adherent effect in solutions which are quite high in protein concentration, even as high as about 5 mg/ml per liter. A typical example of composition is ethanol (1-60% vol/vol), protein to lipid (1:30 to 1:10,000 mol/mol) and buffer salts containing 5 mM to 600 mM NaCl and/or 0.5 mM to 10 mM $CaCl_2$.

The following examples of composition are given for purposes of illustration only and not by way of limitation on the scope of the invention. In the examples, Lysozyme was used as a model protein to investigate the effect of ethyl alcohol for following reasons: (i) Lysozyme is a bacteriolytic protein is under investigation as a therapeutic agent for AIDS, and (ii) detailed structural information is available to investigate structure-stability relationships of lysozyme.

EXAMPLE 1

We have carried out biophysical studies to determine the effect of ethanol on the secondary and tertiary structure of lysozyme as a function of temperature. Far-UV and near-UV circular dichroism (CD) spectrophotometry was used to investigate ethanol dependent changes in conformation. Differential Scanning Calorimetry (DSC) was employed to determine the thermodynamic parameters associated with the unfolding of the protein. ANS (1,8 anilinonaphthalene sulfonate), a fluorescent probe that partitions into hydrophobic domains, was used to detect the exposure of hydrophobic domains that leads to aggregation and precipitation.

The unfolding of the protein using thermal stress in the presence and in the absence of ethanol is carried out to investigate the thermal stability of the protein in ethanol-buffer mixtures. The lyophilized lysozyme (660 ug/ml) was mixed with (20%) ethanol containing phosphate buffered saline (pH 7.4) and the protein was subjected to thermal stress. The conformation and aggregation of the protein was followed by CD and turbidity measurements. As a control experiment, the lysozyme dissolved in phosphate buffered saline in the absence of ethanol was also carried out (FIG. 1). The data shows that the presence of ethanol prevents the formation of aggregates.

In the absence of ethanol, the melting profile was distorted especially at temperatures around 65° C. as indicated in the figure. The turbidity measurements and visual inspection of the sample indicated the presence of aggregates and precipitates of the protein. In the presence of ethanol, the analysis of unfolding profile of the protein indicated that the melting of the protein follows a two state model and the visual inspection of the sample suggested absence of any significant fraction of aggregates or precipitates.

In order to get further insight into the stabilization of protein in low solvent concentrations, we examined the conformation of the protein in the presence of ethanol. In the absence of ethanol, the far UV CD spectrum of the protein displayed two negative bands, one around 220 nm and another more intense band around 208 nm. Qualitative analysis of the data indicates that the secondary structural content of lysozyme is predominantly $\alpha+\beta$ and is consistent with the 3D structure of the protein (8). At lower ethanol concentrations, (<50% v/v), a small decrease in intensity of the CD bands was observed but the shape of the spectra remained unchanged. The data clearly indicates that the lower concentration of ethanol did not induce substantial secondary structure of the protein. However, at higher ethanol concentrations, (>60% vol/vol), a more pronounced increase in intensity of the bands were observed and this intensity change was accompanied by changes in the spectral characteristics (data not shown). Overall, the ratio of the negative bands, 220 nm to 208 nm was closer to unity in solutions containing higher ethanol concentration. This spectral characteristic clearly indicates that higher ethanol concentrations induced more helical structure in the protein. The data contribute to the conclusion that ethanol concentrations below about 60% v/v would not have an appreciably negative effect upon protein function.

EXAMPLE 2

This example describes the effect of ethyl alcohol on tertiary structure. The near-UV CD spectrum is sensitive to the specific orientation of the aromatic groups and tertiary structure. In 100% aqueous, lysozyme displayed three positive bands at 280, 287 and 291 nm; these have been assigned to the transitions of Trp residues. In the presence of lower concentrations of ethanol (<60% vol/vol), enhancement in the CD bands was observed. In addition, it was also observed that the ratio of the positive peaks at 280 and 287 nm was sensitive to the presence of ethanol. However, further increase in ethanol concentrations resulted in the loss of the CD bands, indicating a lack of any appreciable tertiary structure (data not shown).

Based on the CD results, it is clear that the presence of ethanol at lower concentration has no effect on the secondary structure but displayed a slight increase in the intensity of the near UV bands. Such increase in near UV CD bands may possibly be due to the stabilization of the native state by solvents. Preferential hydration is a thermodynamic phenomenon that reflects the inability of organic molecules to interact with the proteins and this leads to the exclusion of the organic solvents. It has also been shown that such stabilization increases the phase transition temperature. In order to determine the mechanism of solvent mediated stabilization of proteins against aggregation, thermal transition profiles were obtained. In aqueous medium, the Tm of the protein was observed around 74.3° C. and is consistent with CD studies and other reported results (8). Further analysis of the data revealed that the melting temperature (Tm) and calorimetric enthalpy ($\Delta H_{cal}$) were dependent on ethanol concentrations; as the ethanol concentration was increased from 0 to 20% vol/vol, both the Tm and $\Delta H_{cal}$ decreased. The observed decrease in Tm may be due to the favorable interaction of the solvent molecule with the exposed hydrophobic domains of the unfolded protein.

EXAMPLE 3

In order to determine the exposure of hydrophobic domains associated with the unfolding of the protein, the binding of fluorescence probes such as 1,8 anilinonaphthalene sulfonate (ANS) was investigated. In aqueous medium, the fluorescence intensity of the probe increased as the protein unfolded indicating the exposure of hydrophobic domains as the protein unfolded. The estimation of the Tm based on such profile was around 74° C. and is consistent with thermal denaturation studies and previously published results. But in the presence of low concentrations of ethanol, the Tm and exposure of hydrophobic domains was found to occur at lower temperature. For example, at 50° C., the fluorescence intensity of the probe bound to protein in aqueous environment increased by 10% over that of the unfolded state, whereas the presence of 20% ethanol the fluorescence intensity of the probe increased by 30%. In order to account for the contribution of solvent enhanced fluorescence, the initial fluorescence intensity of the probe was normalized and the temperature dependent effects were calculated as percent change rather than absolute fluorescence intensity. The decrease in Tm and exposure of hydrophobic domains in solvent containing solutions is possibly because as the protein unfolds, hydrophobic residues come into contact with clusters of solvent molecules, thus thermodynamically favoring the exposure of hydrophobic domains. But such exposure of hydrophobic domains in aqueous environment may lead to aggregation of the protein.

Since the exposure of hydrophobic domains lead to the aggregation of the protein, clustering of solvent molecules around the hydrophobic residues prevent the aggregation (FIG. 1). In case the processing and storage of freeze dried protein results in denaturation of the protein, the reconstitution medium containing low solvent concentrations may prevent the surface adsorption and aggregation of the protein. Further, denaturation during reconstitution due to agitation, shaking, formation of foam and froth and the contact of the protein with air-aqueous interfaces may be minimized by solvent exposure. The combination of solvent and specific ions may also promote the refolding of the protein to the native conformation (data not shown) as the role of specific ions in the refolding process is well documented.

The data lend support to the conclusion that the presence of small quantities of the solvent minimize the denaturation and aggregation by clustering around the hydrophobic residues of the unfolded protein, and low levels of alcohol can prevent aggregation of denatured protein.

EXAMPLE 4

This example describes the effect of reconstitution medium (solvent and buffer salts) on lipid structure. In order to determine the effect of ethanol containing buffer system on the structure and dynamics of liposomal structures, DSC thermal profiles in the presence and in the absence of ethanol was carried out. In the absence of ethanol, the main transition temperature was observed at 23° C. and is consistent with the previous studies reported by others. In the presence of ethanol, the transition peak was broadened and a shift in the temperature was observed. Such effects are consistent with ethanol inducing packing defects in the bilayer organization, and thus lend support for the conclusion that ethanol induces such packing defects. The effect of ethanol on protein appears to be to expose the hydrophobic domains and it influences the packing defects in bilayer. This effect can promote the interaction of protein (exposed hydrophobic domains) with lipid bilayer (packing defects) increasing the encapsulation efficiency of proteins in liposomes.

EXAMPLE 5

Figure 2:
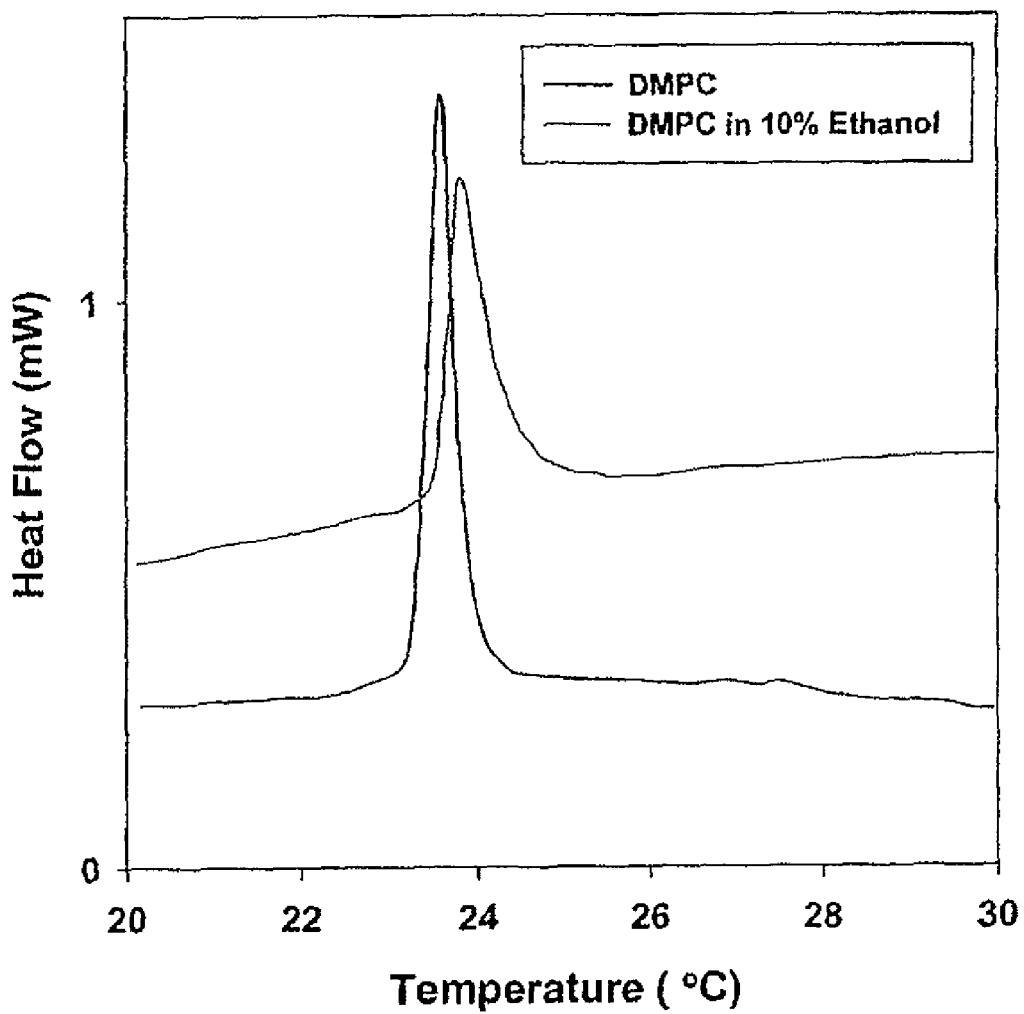
FIG. 2 displays the interaction of reconstitution medium with lipid. The Differential Scanning Calorimetry (DSC) profile of Dimyristoyl Phosphatidylcholine (DMPC) vesicle in the presence and in the absence of 10% ethanol in phosphate buffered saline.

The effect of ethanol on the bilayer structure and dynamics of Dimyristoyl Phosphatidylcholine was carried out. 6.84 mg of DMPC dissolved in chloroform, was evaporated to form a thin dry film on the walls of a round bottom flask or Kimax tubes. The dry film was rehydrated in 10% ethanol and phosphate buffered saline (FIG. 2). The addition of ethanol to DMPC vesicles resulted in the shift and broadening of the main transition temperature indicating that ethanol causes packing defects of the bilayer.

EXAMPLE 6

Figure 3:
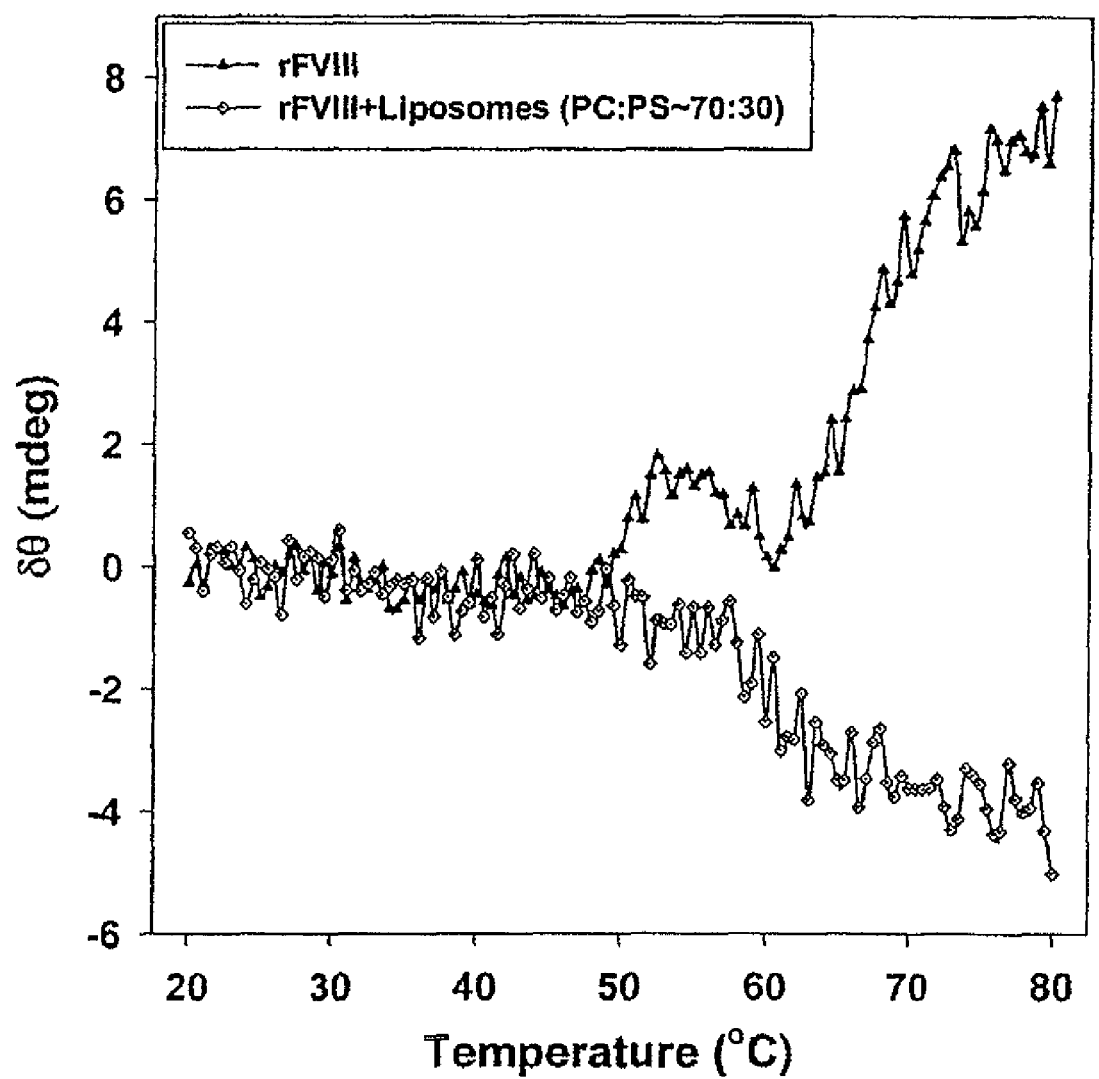
FIG. 3 displays the effect of reconstitution medium on both lipid and protein. The circular dichroism (CD) melting profile of Factor VIII (5 mM CaCl2 and 100 mM NaCl) in the presence and in the absence of lipid, Phosphatidylserine. The CD spectra were acquired with a heating rate of 15° C./hr.

The physical stability and aggregation of 20 ug/ml of FVIII was monitored in the presence of PS in 25 mM TRIS, $CaCl_2$ and 100-300 mM NaCl. The conformation and aggregation of the protein was followed by CD measurements (FIG. 3). In the presence of lipid, the aggregation of Factor VIII was reduced.

EXAMPLE 7

This example shows the effect of calcium on the formation of cochleate and bilayer structures. PS with shorter chain lipids (less that 12 carbon atoms) tends to form micelles while PS with longer chain lipids (12 or more carbons) tends to form cochleates. Further, in a mixture of PC and PS, if the proportion of PC is more, liposomes and bilayers are preferentially formed.

Figure 4A:
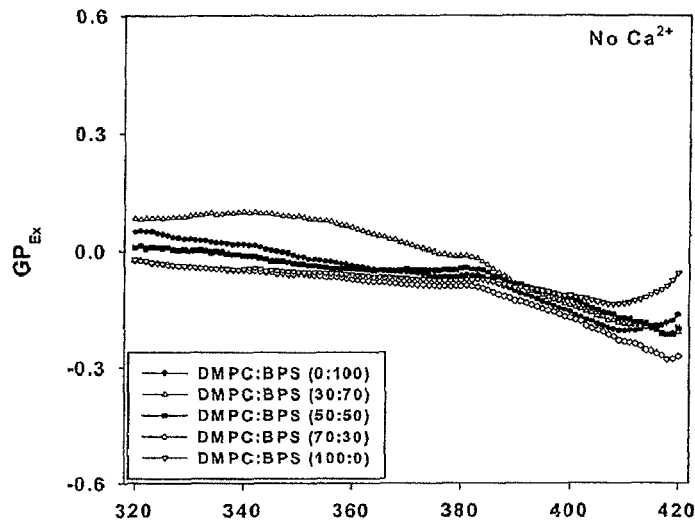
FIGS. 4a-4c displays the effect of reconstitution medium (5 mM $CaCl_2$ and NaCl) on lipidic structures. The LAURDAN profiles of phosphatidylserine containing lipidic particles are shown in the absence of calcium (4a), presence of calcium (4b) and presence of calcium and EDTA (4c).
Figure 4B:
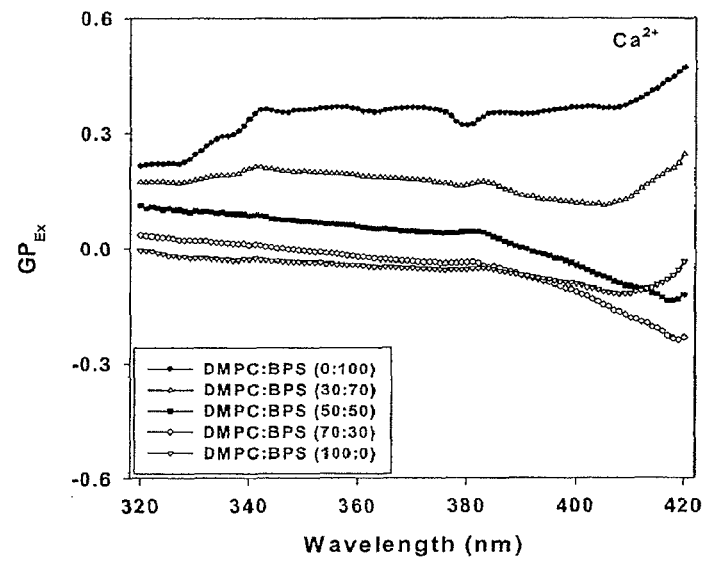
Figure 4C:
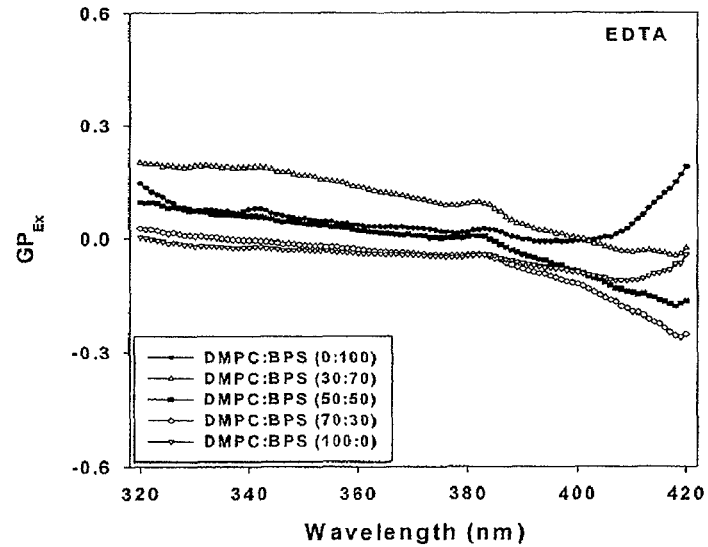

This example shows fluorescence spectra acquired on an SLM 8000C or a PTI Quanta Master spectrofluorometer for cochleate and other bilayer structures (FIG. 4). Emission spectra were acquired over the range of 425 to 550 nm, using a slit width of 4 nm on the excitation and emission paths. Correction for the inner filter effect was performed by appropriate procedures (9). Samples were maintained at the desired temperature using a water bath (Neslab RTE 110, NESLAB Instruments Inc, Newington, N.H.). Spectra were corrected through the use of an internal reference and further processed using software provided by the manufacturer. The effect of $Ca^{2+}$PS interaction was monitored by Laurdan fluorescence. The fluorescence emission spectra of Laurdan was sensitive to the formation of lamellar, cochleate phases (FIG. 4). The presence of $Ca^{2+}$ ions promote the formation of lipid molecular assemblies such as cochleate phases.

EXAMPLE 8

Hen egg-white lysozyme was purchased from Sigma (St Louis Mo.) as a crystallized dialyzed and lyophilized powder (Batch No: 57M7045). Recombinant FVIII was expressed in COS-7 cells and purified by chromatography. The lipids were purchased from Avanti Polar lipids (Alabaster Ala.). Spectroscopy grade solvents were purchased from Pharmaco Inc (Brookfield, Conn.) and used without further purification. ANS (1-anilino-8-naphthalene sulfonate) and Laurdan (a probe of hydrophobic domains) were purchased from Molecular Probes Inc. (Eugene Oreg.). The ethanol-aqueous mixtures were prepared by mixing appropriate volumes of respective solvents and the total volume estimated as described in USP.

EXAMPLE 9

CD spectra were acquired on a JASCO J715 spectropolarimeter calibrated with $d_{10}$ camphor sulfonic acid. Temperature scans were acquired using a Peltier 300 RTS unit and the melting profiles were generated using software provided by the manufacturer. The spectra were acquired at heating rates of 60° C./hr and 15° C./hr. The data presented in FIG. 1 is acquired using 60° C./hr heating rate and for FIG. 3, the heating rate was 15° C./hr. For all the samples, a 10 mm cuvette was used to acquire the data. Samples were scanned in the range of 260 to 200 nm for secondary structural analysis, and the protein concentration used was 20 μg/ml (FIG. 3). For near UV CD studies, the spectra were acquired in the range of 360 to 270 nm, and the protein concentration used was 0.66 mg/ml (FIG. 1). CD spectra of the protein were corrected by subtracting the spectrum of the solvent alone, and multiple scans were acquired and averaged to improve signal quality. The melting profiles were used to determine the stability of the protein.

EXAMPLE 10

A two-state unfolding model was applied to analyze the equilibrium unfolding data. Each unfolding curve was normalized to the apparent fraction of the unfolded form ($F_{app}$), using the relationship:

$$F_{app}=(Y_{obs}-Y_{nat})/(Y_{unf}-Y_{nat})$$

where $Y_{obs}$ is the ellipticity (at 220 nm or 290 nm) at a given temperature, and $Y_{unf}$ and $Y_{nat}$ are the spectral values for unfolded and native structures, respectively. $Y_{unf}$ and $Y_{nat}$ are obtained by performing a linear regression analysis of the spectrum plateau region at high and low temperatures, respectively.

EXAMPLE 11 rFVIII clotting activity was determined by one-stage activated partial thromboplastin time (APTT) assay using micronized silica as activator and FVIII deficient plasma as the substrate. The APTT assay was performed using a COAG-A-MATE coagulation analyzer (Organon Teknika Corporation, Durham, N.C.). Briefly, rFVIII was added to FVIII deficient plasma and the clotting time was monitored. The activity of the rFVIII was then obtained from calibration curve constructed using the clotting times determined from various dilutions of a lyophilized reference concentrate of known activity. The concentration of the protein was determined independently using Bicinchoninic acid (BCA) assay and compared with activity. For example, all the 20-22 μg/ml of the protein corresponds to specific activity of 87-95.6 IU. The stock solution used to prepare the samples had a specific activity of 2174 IU/0.5 mg/ml. The data is shown in FIG. 3. The activity assay showed that the presence of lipidic particles did not alter the activity of Factor VIII.

EXAMPLE 12

ANS (1-anilino-8-naphthalene sulfonate) was dissolved at 1 mg/ml containing 2% ethanol, and a small volume was added to a solution of 10 μM of lysozyme in water, to give a final probe concentration of 0.3 μM. The initial fluorescence intensity of the probe was normalized to account for the general solvent effects of ethanol on fluorescence measurements. The data indicated that the presence of ethanol results in the exposure of hydrophobic domains of the protein.

EXAMPLE 13

Differential Scanning Calorimetric studies were carried out on a Perkin-Elmer DSC-7 instrument with samples sealed in aluminum pans. The instrument was calibrated with standard samples covering a wide range of temperatures. Thermograms were recorded using a heating rate of 5° K/min (FIG. 2). For each thermogram, 14 μL of a 40 mM liposome solution was used. Samples were kept at the initial load temperature (15° C.) for 5 minutes before each experiment. The peak area and thermodynamic parameters were calculated using software options provided by the manufacturer. Ethanol induces changes in the structure and dynamics of bilayer structures.

EXAMPLE 14

The activity of lysozyme was determined by measuring the catalytic activity of the protein as described earlier (10,11). The protein was diluted 20 times into an assay mixture containing a prefiltered cell suspension of 0.16 mg/ml of *M. lysodeikticus* and the change in absorbance at 450 nm was monitored for the bacteriolytic activity of the protein. Control experiments were performed for the relevant ethanol concentrations and the data indicated that the presence of ethanol did not interfere with the activity of the protein.

EXAMPLE 15

The particle size of the aggregated protein was determined using NICOMP 315 particle sizer and the turbidity was measured using VARIAN spectrometer. The particle size distribution was analyzed using both Gaussian and NICOMP analysis for unimodal and bimodal distribution. The size of the standard latex beads were measured prior to each measurement. For turbidity measurements, the OD at 350 nm was followed as function of temperature.

EXAMPLE 16

The relative fraction of aggregated protein was determined using size exclusion chromatography (SEC). High Performance Size Exclusion Chromatography (HP-SEC) was performed using Biosep SEC S4000 (4.6 mm×300 mm). The analytical column was maintained at 20° C. using a Shimadzu CT0-10AC column oven. Chromatograph comprised of a Waters 510 HPLC Pump, Rheodyne injector with a 50 µl PEEK sample loop and Hitachi F1050 fluorescence detector. Elution of protein was monitored using the intrinsic fluorescence of rFVIII. Excitation and emission were set at 285 nm and 335 nm respectively to monitor the elution of the protein. Gel filtration was carried out under isocratic conditions at a flow rate of 0.4 ml/min using an aqueous buffer consisting of 25 mM Tris, 5 mM $CaCl_2$ and 300 mM NaCl, pH=7.0. The exclusion volume for the column used eluted out at 5.1 minutes as determined using aggregated protein standard.

EXAMPLE 17

This example describes the formation of lipid molecular assemblies such as micelle formation in the absence of protein after reconstitution using $Ca^{2+}$ ions in the reconstitution medium which does not contain alcohol. The formation of lipid molecular assemblies such as micelle formation were monitored using diphenyl-1-3-5-hexatriene (DPH) fluorescence. DPH fluorescence was measured using a PTI-Quantamaster fluorescence spectrophotometer (Photon Technology International, Lawrenceville, N.J.) at $\lambda_{excitation}$ of 360 nm and $\lambda_{emission}$ of 430 nm. Excitation and emission slit widths were set at 2 nm. A variable path length cuvette was used to minimize the inner filter effect. Samples were also monitored using a Submicron Particle Sizer, Nicomp-380 (Particle Sizing Systems, Santa Barbara, Calif.) to determine the particle size and detect presence of micelles at low concentrations of lipid not detectable by DPH fluorescence. Data Analysis: DPH fluorescence intensity was plotted against the concentration of lipid. Individual linear regressions were performed for the two linear portions of the plots (before and after CMC) and linear equations were obtained. The point of intersection of these two lines is the CMC for the lipid. The CMC was obtained using the following expression:

$$CMC = \frac{C_2 - C_1}{m_1 - m_2}$$

Where, $C_1$, $C_2$ are intercepts and $m_1$, $m_2$ are the slopes obtained from each individual regression performed on the data.

The aqueous buffer was comprised of 25 mM tris, 300 mM NaCl and 5 mM $CaCl_2$ (Tris buffer). Calcium chloride was excluded from the buffer for experiments conducted with no $Ca^{2+}$ ions. Aqueous solutions of dried DCPS (1 ml) containing various concentrations of lipid (1.0, 2.0, 2.5, 3.0, 3.5, and 4.0 mM) were prepared and mixed with 1 µl of 0.005 M diphenyl-1-3-5-hexatriene (DPH) solution. Use of DPH as a probe to measure CMC depends upon its property to preferentially partition into lipidic structures (vesicles, micelles etc.) with a simultaneous increase in the fluorescence intensity. For lipids having a tendency to form micelles, at lipid concentrations below the CMC the DPH exhibits low fluorescence intensity which is almost independent of lipid concentration. Beyond the CMC, DPH fluorescence intensity increases and shows a strong dependence on lipid concentration (data not shown). The CMC of DCPS as determined using DPH in presence and absence of $Ca^{2+}$ was 2.30 mM and 2.96 mM respectively. Presence of calcium leads to the lowering of DCPS CMC. Also observed in presence of calcium beyond the CMC of DCPS was the formation of a white floccular precipitate which could be very large aggregates of DCPS micelles.

EXAMPLE 18

This example describes the effect of inclusion of protein in the composition of Example 17 on the formation of micelles after reconstitution using $Ca^{2+}$ ions. rFVIII (10 µg/ml) was reconstituted with tris buffer containing appropriate concentrations much below CMC, 50, 100 and 800 µM of DCPS. SEC profile of rFVIII shows a single broad peak at ~7 minutes. Further, rFVIII can interact with DCPS (both molecular and micellar forms) owing to its interaction with phosphoserine head group of DCPS. Interaction of rFVIII with the molecular form of DCPS causes no significant changes in the molecular volume of the protein. The interaction of rFVIII with micellar forms of DCPS would however result in a significant increase in the molecular volume of the protein, which would result in the elution of rFVIII with the exclusion volume in SEC. As determined using particle size analyzer DCPS appears to form micelles above 1 mM concentrations. Hence, at concentrations of 50, 100 and 800 µM DCPS very little change in the SEC profile of rFVIII may be expected. However the SEC profiles of rFVIII in presence of 800 and 100 µM DCPS showed that significant amounts of rFVIII were detected in the exclusion volume. The results from the above studies indicate that interaction of $Ca^{2+}$ and rFVIII with DCPS can reduce the CMC of DCPS. This and the previous example indicate that in the presence of protein lower concentrations of lipid are required to form micelles.

While this invention has been described by using specific embodiments, routine modifications to the methods and compositions described herein will be apparent to those skilled in the art and intended to be within the scope of the present invention.

REFERENCES

1. Ahern, T. J. & Manning, M. C. (eds.). *Stability of protein pharmaceuticals*, 550 (Plenum Press, New York, 1992).
2. Balasubramanian., S. V., Breunn, J. A. & Straubinger, R. M. Liposomes as formulation excipient for protein pharmaceuticals; A model protein study. *Pharmaceutical Research* 17, 343-349 (2000).
3. Manning, M. C., Patel, K. & Borchardt, R. T. Stability of protein pharmaceuticals. *Pharmaceutical Research* 6, 903-918 (1989).
4. Braun, A., Kwee, L., Labow, M. A. & Alsenz, J. Protein aggregates seem to play a key role among the parameters influencing the antigenicity of interferon alpha (IFN-alpha) in normal and transgenic mice. *Pharm Res* 14, 1472-8 (1997).
5. Singh, M. & Ravin, L. J. Parenteral emulsions as drug carrier systems. *J Parenter Sci Technol* 40, 34-41 (1986).

6. Spiegel, A. J. & Noseworthy, M. M. Use of Nonaqueous Solvents in Parenteral products. *J. Pharm. Sci.*, 917-926 (1963).
7. Wang, Y. C. & Kowal, R. R. Review of excipients and pH's for parenteral products used in the United States. *J Parenter Drug Assoc* 34, 452-62 (1980).
8. Knubovets, T., Osterhout, J. J., Connolly, P. J. & Klibanov, A. M. Structure, thermostability, and conformational flexibility of hen egg-white lysozyme dissolved in glycerol. *Proc Natl Acad Sci USA* 96, 1262-7 (1999).
9. Lakowicz, J. R. *Principles of Fluorescence Spectroscopy*, (Plenum Press, New York, 1986).
10. Rariy, R. V. & Klibanov, A. M. Protein refolding in predominantly organic media markedly enhanced by common salts. *Biotechnol Bioeng* 62, 704-10 (1999).
11. Rariy, R. V. & Klibanov, A. M. Correct protein folding in glycerol. *Proc Natl Acad Sci USA* 94, 13520-3 (1997).

What is claimed is:

1. A method for reconstitution of a dry protein preparation to produce a stabilized reconstituted protein solution, said method comprising:
   a) providing
      i) a dry protein preparation, and
      ii) a reconstitution medium comprising ethanol, wherein the ethanol is less than 60% of the reconstitution medium by volume, and wherein the reconstitution medium is buffered to a physiological pH,
         wherein i) and/or ii) comprise lipids, wherein the lipids are selected from the group consisting of phosphatidyl serine, phosphatidyl choline, and combinations thereof; and
   b) combining i) and ii) to form a stabilized reconstituted protein solution in which less than 30% of the protein is present in the form of aggregates as determined by size-exclusion chromatography.

2. A method as in claim 1 wherein the protein in the stabilized reconstituted protein solution maintains its tertiary structure as evidenced by circular dichroism.

3. A method as in claim 1 wherein the concentration of the one or more lipids is in the range of from 0.3 mM to 40 mM.

4. A method as in claim 1 wherein the buffer in the reconstitution medium comprises calcium ions.

5. A method as in claim 4 wherein the buffer concentration is 0.5 mM to 600 mM.

6. A method as in claim 1 wherein said dry protein preparation contains one or more lipid components selected from the group consisting of liposomes, micelles, cochleates, laminar, and lamellar structures, and combinations thereof, which are associated with the protein.

7. A method as in claim 1 wherein the dry protein preparation comprises Factor VIII.

8. A method as in claim 1 wherein the concentration of the ethanol is less than 20% by volume.

9. A method as in claim 8 wherein the concentration of the one or more alcohols in the stabilized reconstituted protein solution is in the range of from 5% by volume to 10% by volume.

10. The method of claim 1, wherein the physiological pH is 7.2.

11. The method of claim 1, wherein the protein has an accessible hydrophobic domain.

* * * * *

UNITED STATES PATENT AND TRADEMARK OFFICE
CERTIFICATE OF CORRECTION

PATENT NO. : 8,349,794 B2
APPLICATION NO. : 12/204922
DATED : January 8, 2013
INVENTOR(S) : Balasubramanian Page 1 of 1

It is certified that error appears in the above-identified patent and that said Letters Patent is hereby corrected as shown below:

In the Specification

Column 1, Lines 9-11 should read:
--STATEMENT REGARDING FEDERALLY SPONSORED RESEARCH
This invention was made with government support under RO1 HL070227-01 awarded by
the National Institutes of Health. The government has certain rights in the invention.--

Signed and Sealed this
Twenty-third Day of September, 2025

John A. Squires
*Director of the United States Patent and Trademark Office*